United States Patent [19]

Mäki et al.

[11] 4,169,840
[45] Oct. 2, 1979

[54] METHOD OF PREPARING FUROCOUMARINS

[75] Inventors: Juhani I. T. Mäki, Porvoo; Pentti J. Mälkönen, Vantaa; Heikki E. Nupponen, Kangasala, all of Finland

[73] Assignee: Oy Star AB, Tampere, Finland

[21] Appl. No.: 850,868

[22] Filed: Nov. 14, 1977

[30] Foreign Application Priority Data

Oct. 3, 1977 [FI] Finland ............................. 772899

[51] Int. Cl.$^2$ ............................................ C07D 493/04
[52] U.S. Cl. ......................... 260/343.21; 260/343.44
[58] Field of Search ...................... 260/343.21, 343.44, 260/346.22

[56] References Cited

U.S. PATENT DOCUMENTS

| 2,889,337 | 6/1959 | Stanley et al. | 260/343.44 |
| 3,201,421 | 8/1965 | Kaufman | 260/343.21 |
| 3,862,134 | 1/1975 | Scherrer | 260/346.22 |

OTHER PUBLICATIONS

Bradsher, Chemical Reviews, vol. 38, 1946.

Primary Examiner—Natalie Trousof
Assistant Examiner—Jane T. Fan
Attorney, Agent, or Firm—A. C. Nolte, Jr.; Edward B. Hunter

[57] ABSTRACT

This invention relates to an improved method of preparing furocoumarins having the following formula:

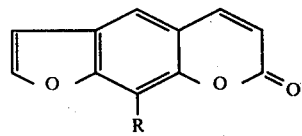

wherein R is a radical selected from the group consisting of hydrogen, hydroxy and lower alkoxy, which comprises reacting a coumarin having the following formula:

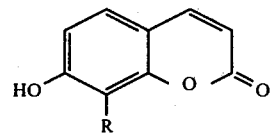

or the alkali metal salt thereof, with a haloacetal having the following formula:

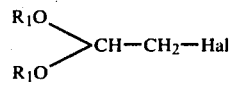

wherein $R_1$ is a lower alkyl group and Hal is selected from the group consisting of chlorine and bromine; and to the intermediate products thereof, namely a substituted coumarin acetal of the following formula:

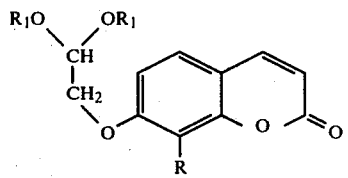

and the corresponding coumarin aldehyde of the following formula:

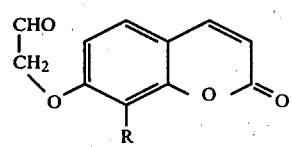

2 Claims, No Drawings

METHOD OF PREPARING FUROCOUMARINS

The object of the present invention is a method of preparing pharmacologically valuable furocoumarins substituted in their 8-position and having the general formula

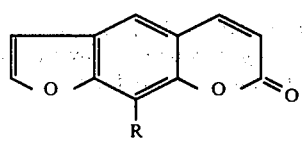

wherein R is selected from the group consisting of hydrogen, a hydroxy group and a lower alkoxy group. R is preferably a methoxy group. The compounds of the formula I are found in small amounts in certain plant species (Ammi majus etc) from which they have been isolated for pharmacological purposes.

Pharmacologically most important furocoumarins of the present invention are the compounds of the formula I wherein R is a methoxy group or hydrogen, and which are known as methoxalene (=xanthotoxine) and psoralene. Compounds of the formula I i.a. methoxalene have been synthesized but with very low yields and utilizing methods, the application of which on an industrial scale is difficult (cf. Lagercrantz: Acta Chem. Scand. 10, 647–654 (1956); Rodighiero et al.: Annal. Chimica 46, 960–67 (1956); Seshadri et al.: Indian J. Chem. 1 (7), 291–4 (1963); de Souza et al.: J. Heterocycl. Chem. 3, 42–5 (1966); Chatterjee et al.: Tetrahedron Letters 59, 5223–4 (1969) and others).

The compounds of the formula I are prepared by using as starting materials substituted coumarins of the general formula

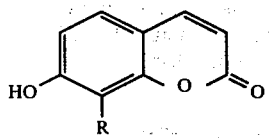

wherein R denotes the same as in the formula I and which may be prepared according to methods known from literature. By reacting the coumarin according to formula II, or preferably its alkali metal salt, with a haloacetal of the general formula

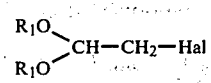

wherein $R_1$ is a lower alkyl group and Hal is selected from the group consisting of chlorine and bromine, in an inert solvent or solvent mixture, a substituted coumarin acetal of the formula IV is obtained, which may be converted into the corresponding aldehyde (formula V) by heating in a dilute acid solution. In order to prepare the end product, the aldehyde is ring-closed by heating in a dilute alkaline solution. The reaction may be illustrated by the following scheme:

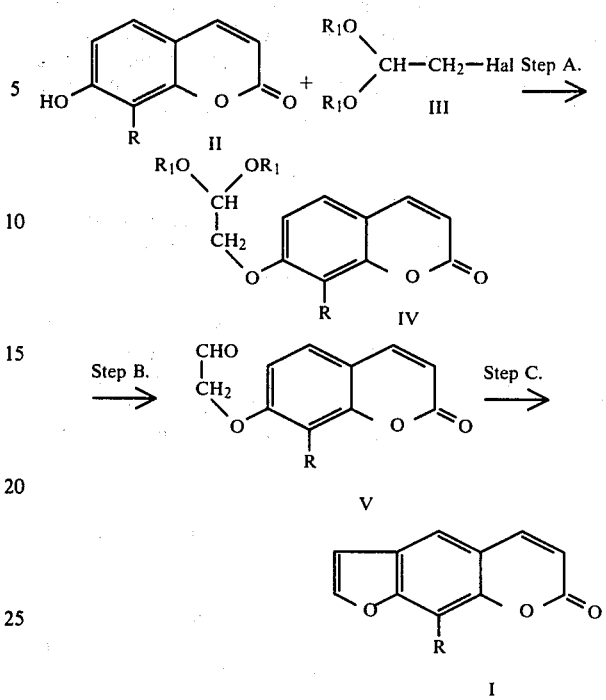

wherein R, $R_1$ and Hal denote the same as before.

The reaction step A is carried out by heating the compound II or preferably its sodium salt and the compound III in an inert, anhydrous, organic solvent or solvent mixture for 2 to 48 hours at a temperature of 70° to 170° C. It is advantageous to use a mixture of tetrahydrofuran and dimethylformamide and to boil for 24 hours, or to use dimethylformamide and a reaction time of 8 hours.

In steps B and C the heating time may vary between 15 min and about 4 hours. The method is also easily applicable on an industrial scale, whereby steps B and C may be combined (c.f. Example 2). The overall yield of the synthesis is about 50% of the theoretical value, whereas in prior methods it has been at the most about 8%.

The intermediate compounds IV and V obtained above in the reaction steps A and B are new compounds per se, and fall as such within the scope of the invention.

All intermediate and end products have been indentified by means of NMR, IR and mass spectra as well as melting points and elementary analysis and their purity has been determined by thin layer chromatography.

The following Examples illustrate the present invention.

EXAMPLE 1

Step A 19.2 g (=0,1 moles) of 7-hydroxy-8-methoxy-coumarin are dissolved in 70 ml of anhydrous tetrahydrofuran and 5.05 g of a 50% NaH-dispersion in oil are added and the mixture is boiled under reflux while stirring for about 30 min. To the mixture is added while stirring 23.6 g (=0.12 moles) of bromoacetaldehyde-diethylacetal (=bromoacetal) dissolved in 140 ml of anhydrous dimethylformamide and the mixture is boiled under reflux while stirring for 24 hours. The mixture is cooled and ether and water is added. The ether phase is separated and the aqueous phase washed with ether. The etherous extracts are combined and washed with water, a dilute K₂CO₃-solution and water and dried and evaporated to a small volume and cooled, whereby the acetal precipitates. This is separated by filtration and washed with cold ether and dried, whereby about 18.5 g (=60% of the theoretical) of the product are obtained, which, if desired, may be recrystallized from ether, m.p. 91°-3° C.

Step B

The acetal obtained above is converted into the corresponding aldehyde in the following manner:

30.8 g (=0.1 moles) of raw product are boiled under reflux while stirring for 1.5 hours in a 0.1 normal H₂SO₄-solution and is cooled, whereby the aldehyde precipitates. The product is separated by filtration and washed with water and dried. The yield is about 22 g (=87% of the theoretical) of a colourless product, m.p. 110°-12° C. (from acetone; contains 1 mole of crystal water).

Step C

The furocoumarin (=methoxalene; R=—OCH₃) of the formula I may be prepared from the aldehyde obtained above in the following manner:

23.4 g (=0.1 moles) of aldehyde are heated under reflux while stirring for 30 min in a 0.1 normal NaOH-solution and is cooled and acidified with dilute H₃PO₄, whereby a light yellow, milklike solution is obtained. The solution is extracted with CHCl₃ and the extract evaporated to dryness in vacuum. The solid residue is recrystallized from methanol. The yield is about 18.5 g (=85% of the theoretical) of a colourless product, m.p. 147°-8° C.

EXAMPLE 2

The reaction is carried out as in Example 1, but the steps B and C are combined so that the acid reaction mixture after boiling for 1.5 hours is neutralized and made 0.1 normal as to NaOH and is further boiled for 30 min. The end product is isolated according to Example 1, step C.

EXAMPLE 3

By carrying out the reaction as in Example 1, but by using as a starting material 7-hydroxy-coumarin (formula II, R=H) an end product according to the formula I is obtained (R=H) named psoralene, m.p. 160°-2° C., yield 85%.

EXAMPLE 4

By carrying out the reaction as in Example 1, step A, but by using as a starting material 7-hydroxy-coumarin (formula II, R=H) and dimethylformamide as a solvent and a reaction time of 8 hours at 150° C., the acetale according to formula IV is obtained (R=H) with yield of about 75%, m.p. 62°-4° C. (from ether).

According to Example 1, step B, this acetal may be converted to the aldehyde of the formula V, m.p. 118°-20° C. (contains 1 mole of crystal water) with a yield of 95%.

We claim:

1. Method of preparing a furocoumarin of the formula

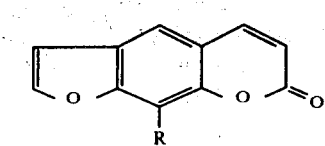

wherein R is selected from the group consisting of hydrogen, a hydroxyl group and a lower alkoxy group, characterized in that a substituted coumarin of the formula

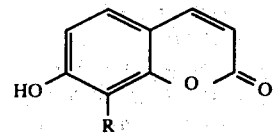

wherein R denotes the same as before, or an alkali metal salt thereof is reacted with a haloacetal of the formula

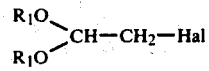

wherein $R_1$ is a lower alkyl group and Hal is selected from the group consisting of chlorine and bromine, in an inert, anhydrous organic solvent or solvent mixture, to obtain an intermediate product of the formula

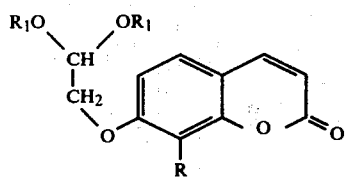

wherein R and $R_1$ denote the same as before, which is treated with a dilute acid at an elevated temperature, to obtain a compound of the formula

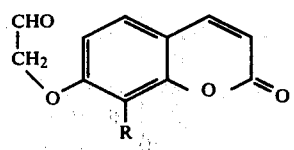

wherein R denotes the same as before, which is converted into the end product of the formula I by heating with a dilute alkaline solution, and acidfying said end product.

2. Method according to claim 1, characterized in that the compound of the formula IV is converted directly into the desired end product of the formula I by heating first in an acid and thereafter in an alkaline solution.

* * * * *